US005494162A

United States Patent [19]
Treace et al.

[11] Patent Number: 5,494,162
[45] Date of Patent: Feb. 27, 1996

[54] PACKAGE AND METHOD FOR DELIVERING A MEDICAL IMPLANT

[75] Inventors: Dan H. Treace; F. Barry Bays, both of Clearwater, Fla.

[73] Assignee: TreBay Medical Corporation, Clearwater, Fla.

[21] Appl. No.: 344,700

[22] Filed: Nov. 18, 1994

[51] Int. Cl.$^6$ .................................................. A61B 19/00
[52] U.S. Cl. .......................................... 206/438; 206/493
[58] Field of Search ................................... 206/438, 363, 206/370, 439, 493

[56] References Cited

U.S. PATENT DOCUMENTS

| | | | |
|---|---|---|---|
| 4,332,322 | 6/1982 | Jaeschke et al. | 206/363 X |
| 4,750,619 | 6/1988 | Cohen et al. | 206/438 |
| 5,394,983 | 3/1995 | Latulippe et al. | 206/370 |
| 5,405,005 | 4/1995 | White | 206/438 X |

OTHER PUBLICATIONS

"Photocopy of Prior Art Package sold by Richards Medical Company of Memphis, TN.".

Primary Examiner—Jacob K. Ackun

[57] ABSTRACT

A package for sterile delivery of medical implants such as vent tubes includes a compartmented tray, a lid connected with the tray by a living hinge, and one or more posts projecting from a bottom wall of one of the compartments for retaining a medical implant in a substantially fixed position. A groove can also be formed in the tray for aligning a forceps with the medical implant to facilitate grasping and removal of the medical implant.

15 Claims, 6 Drawing Sheets

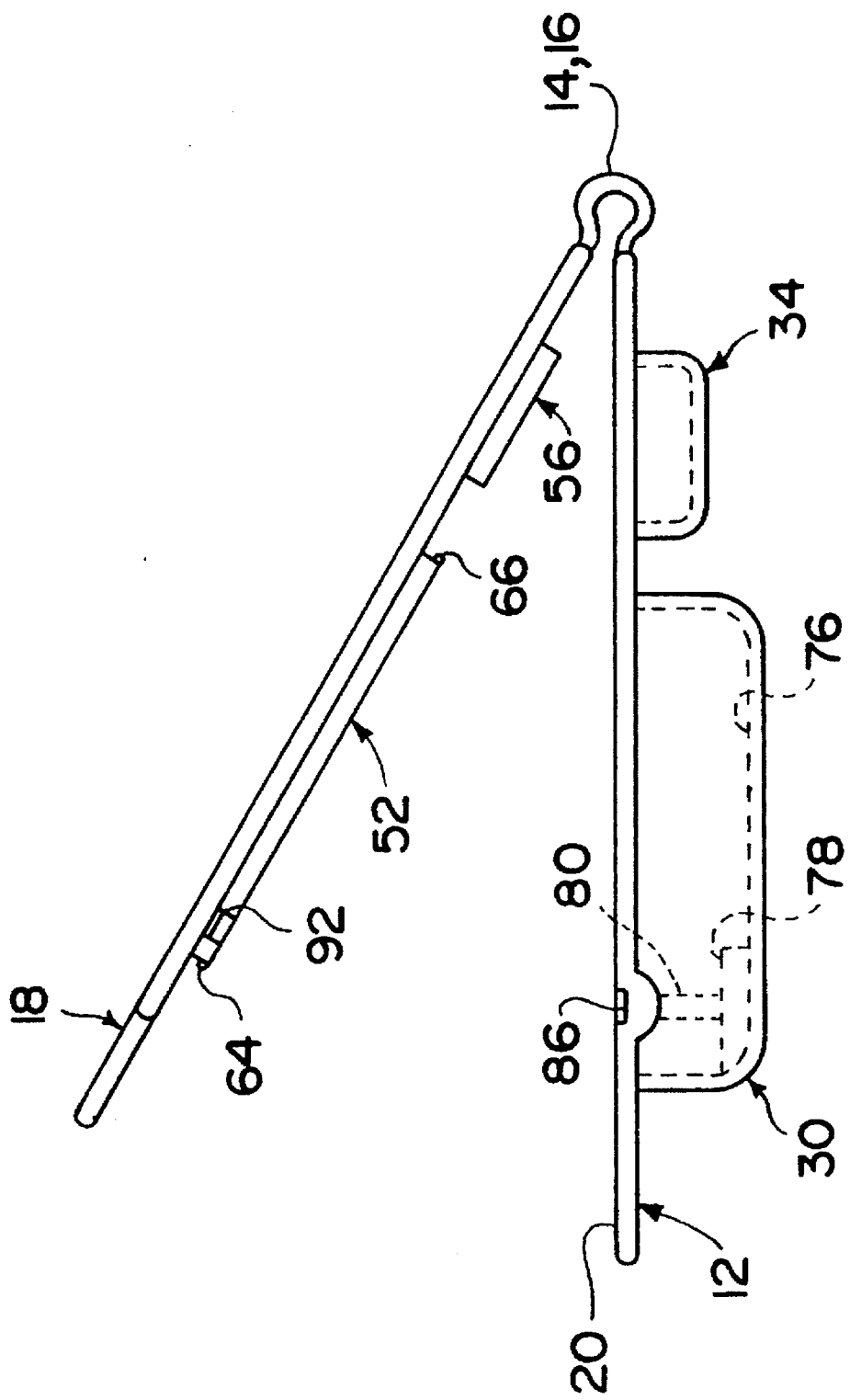

PACKAGE AND METHOD FOR DELIVERING A MEDICAL IMPLANT

BACKGROUND OF THE INVENTION

1. Field of the Invention

The present invention relates generally to packaging and methods for sterile delivery of small medical implants and, more particularly, to a package and method for sterile delivery of tympanotomy vent tubes.

2. Description of the Prior Art

Small medical implants, such as tympanotomy vent tubes implanted in the tympanic membrane of the middle ear as part of a myringotomy, are typically delivered to medical personnel in molded packages having a plurality of cavities or compartments and a lid for closing the compartments. The vent tubes are spool-shaped with round flanges at opposite ends of a cylindrical body and are not restrained within the compartments but, rather, are free to move about when the package is opened. A forceps is normally used for grasping a tube out of one of the compartments for use during the operative procedure; however, this is a difficult and time consuming maneuver because the vent tubes are small and free to move about or float within the compartment and because it is preferable to grasp the tubes with the forceps jaws engaging one flange such that the forceps can be used to insert the opposing flange of the vent tube directly into a slit in the tympanic membrane.

SUMMARY OF THE INVENTION

Accordingly, it is a primary object of the present invention to overcome the disadvantages of the prior art and to facilitate removal of small medical implants from a sterile delivery package.

Another object of the present invention is to limit movement of a small medical implant in a compartment of a sterile delivery package.

Yet another object of the present invention is to guide a forceps into a compartment of a sterile delivery package to simplify extraction of a small medical implant from within the compartment.

It is a further object of the present invention to mount a small medical implant in a vertical upright position within a compartment of a sterile delivery package to facilitate grasping of the medical implant with a forceps.

Some advantages of the present invention over the prior art are that the package of the present invention prevents excessive movement of small medical implants such as vent tubes during transport, sterilization and delivery of the tubes, that quick removal of small medical implants from the package is more adequately assured, and that the package is configured to guide and stabilize a forceps to facilitate grasping of a flange of a medical implant with the jaws of the forceps.

The present invention is generally characterized in a medical implant and a package for sterile delivery of the medical implant including a compartmented tray covered by a lid and means for retaining the medical implant in a substantially fixed position within one of the compartments of the tray during transport and removal, the medical implant being spaced from one side of the compartment by the retaining means to define a space for accommodating jaws of a forceps. In various embodiments of the invention, the medical implant is retained in a substantially fixed position by one or more posts extending from a bottom wall of the compartment and engaging the medical implant. If the medical implant is retained by plural posts, a nub can be carried by the lid in opposed relation to the implant to hold the implant between the posts. In addition, a groove can be formed in the tray on the side of the compartment opposite the medical implant for aligning a forceps with the implant.

Another aspect of the present invention is generally characterized in a method for sterile delivery of a medical implant including the steps of retaining the medical implant in a substantially fixed position within a compartment of a sterile delivery package wherein the medical implant is spaced from one side of the compartment to define a space for accommodating jaws of a forceps, maintaining the package in a horizontal position, aligning jaws of a forceps with the medical implant, grasping the medical implant with the forceps and lifting the medical implant out of the compartment.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 2 is a side view of the package of FIG. 1.

DETAILED DESCRIPTION OF THE PREFERRED EMBODIMENT

Figure 1:
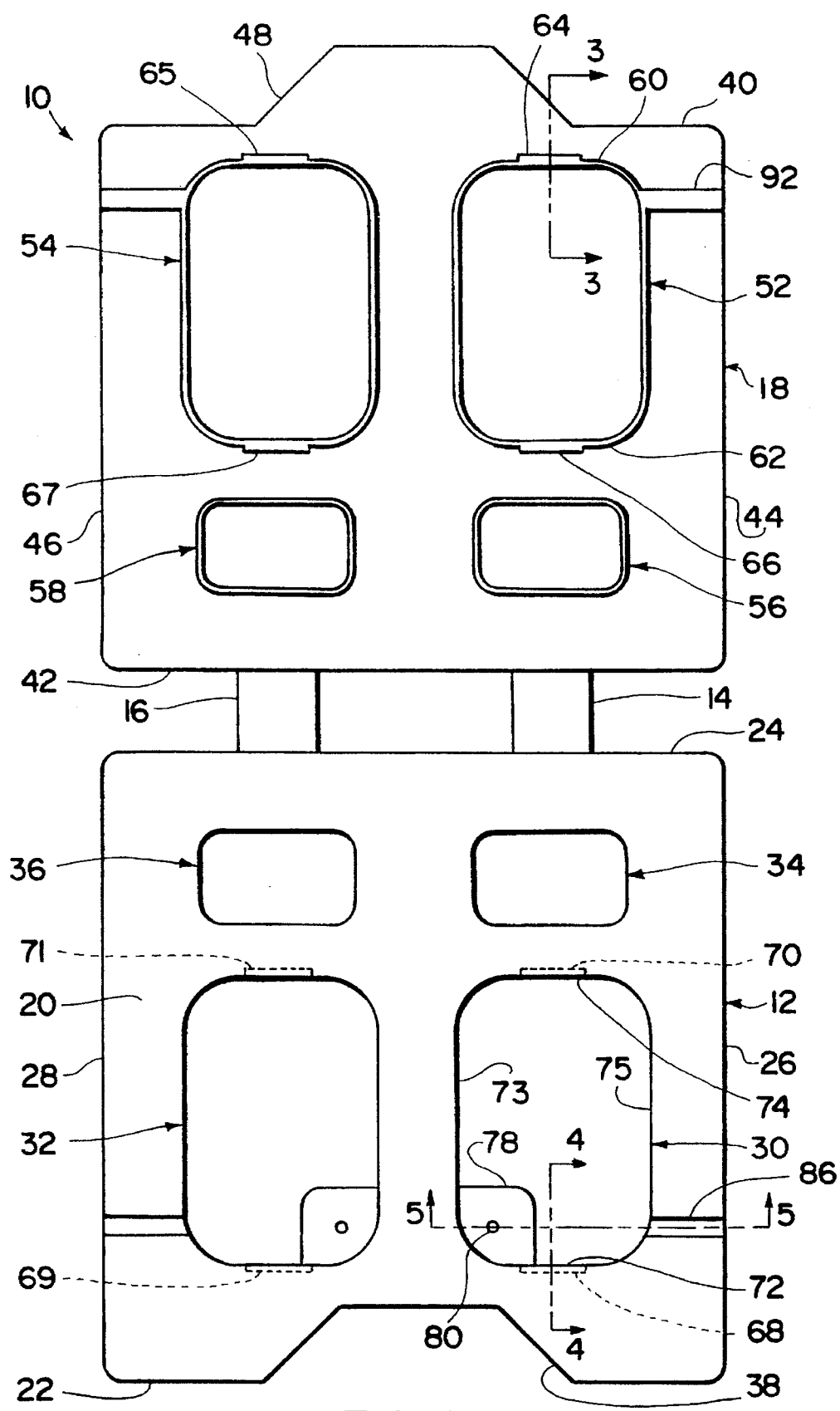
FIG. 1 is a flattened projection of a package according to the present invention.

The package of the present invention is described hereinafter for use in delivering tympanotomy vent tubes in sterile condition. It is understood, however, that the package of the present invention can be used for sterile delivery of any tubular implant or medical device normally grasped using forceps during a medical procedure.

A package 10 according to the present invention is illustrated in FIGS. 1–5. The package 10 is preferably formed as an integral one-piece unit and includes a compartmented tray 12 and a pair of spaced living hinges 14 and 16 connecting the compartmented tray with a lid 18. Tray 12 includes a generally rectangular and flat upper surface 20 having front and rear edges 22 and 24 and opposed lateral edges 26 and 28. A plurality of box-like depressions or compartments 30, 32, 34 and 36 are recessed in the upper surface 20 and define cavities for holding vent tubes of various shapes and sizes as well as other types of medical devices. A trapezoidal cutout 38 is centrally formed along the front edge 22 and extends toward the compartments of the tray.

Hinges 14 and 16 are equally spaced from opposed lateral edges 26 and 28 and extend perpendicularly from the rear edge 24 to connect with lid 18. As best seen in FIG. 2, hinges 14 and 16 are relatively thin arcuate bands integrally formed with the tray 12 and lid 18.

Lid 18 is generally rectangular with front and rear edges 40 and 42 and opposed lateral edges 44 and 46. The distance between front and rear edges of the lid 18 is approximately equal to the distance between the rear edge 24 of the tray and the inner edge of the trapezoidal cutout 38 at the front edge 22 of the tray. A trapezoidal extension 48 approximately equal in size to trapezoidal cutout 38 is centrally formed along the front edge 40 of the lid to partly cover the trapezoidal cutout 38 when the lid 18 is closed against the tray 12. An inner face 50 of lid 18 carries a plurality of elevated ridge formations 52, 54, 56 and 58 configured to fit snugly within compartments 30, 32, 34 and 36. As best seen in FIG. 1, front and rear edges 60 and 62 of elevated ridge 52 carry latching protrusions 64 and 66, respectively, at locations to mate with horizontal pockets 68 and 70 formed in front and rear walls 72 and 74 of compartment 30. Elevated ridge 54 carries similar protrusions 65 and 67 for mating with pockets 69 and 71 in compartment 32. protrusion 64 and pocket 68 are typical of all the mating protrusions and pockets and are illustrated in greater detail in FIGS. 3 and 4, respectively.

The tray 12, lid 18 and compartments 30, 32, 34 and 36, as thus far described, form a conventional package for sterile delivery of vent tubes wherein the vent tubes, such as tympanotomy vent tubes, move about in the compartments in an unrestrained manner, making grasping of the tubes with forceps a difficult task. Exemplary of such prior art packages is the package sold by Richards Medical Company of Memphis, Tenn., for sterile delivery of tympanotomy vent tubes.

In accordance with the present invention, the tray 12 and lid 18 of a conventional package are modified in order to overcome the disadvantages of prior art packages. The package shown is laterally symmetrical with the exception of the depth of compartments 34 and 36; and, accordingly, only one side of the lid 18 and tray 12 will hereinafter be described where such symmetry exists.

Figure 5:
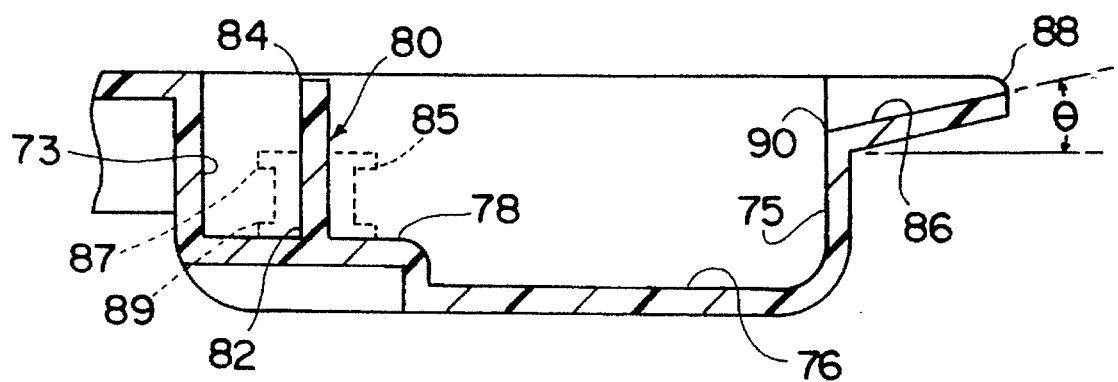
FIG. 5 is a fragmentary cross-sectional view taken through line 5—5 in FIG. 1.
Figure 3:
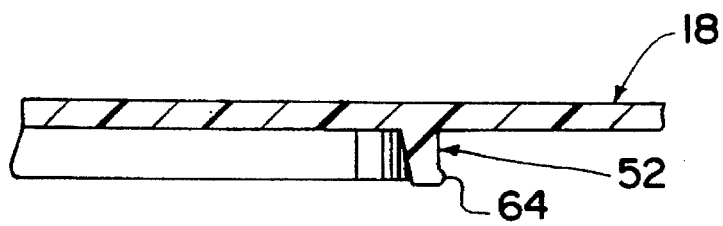
FIG. 3 is a fragmentary cross-sectional view taken through line 3—3 in FIG. 1.
Figure 4:
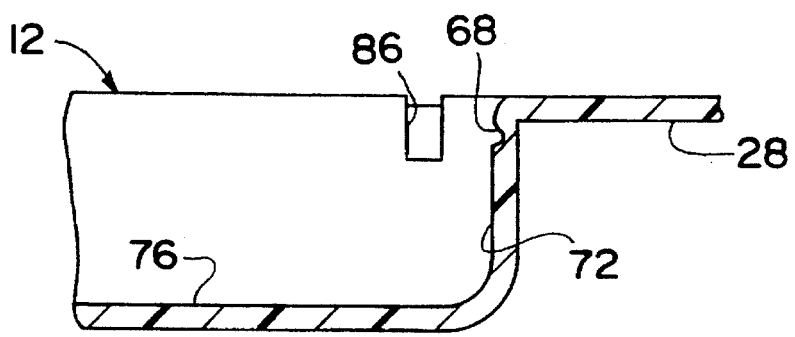
FIG. 4 is a fragmentary cross-sectional view taken through line 4—4 in FIG. 1.

Compartment 30 in tray 12 of the present invention is a generally rectangular depression with rounded corners and front and rear walls 72 and 74, inner and outer side walls 73 and 75, and a bottom wall 76. A portion of the bottom wall 76 is raised to form a horizontal elevation or platform 78 proximate an inner corner of the compartment nearest the trapezoidal cutout 38. The platform 78 is generally rectangular and extends part way along front wall 72 and inner side wall 73. A pin or post 80 is mounted perpendicularly on the platform 78 and is suitably spaced from outer side wall 75 to provide clearance for jaws of a forceps to be positioned alongside the post within the compartment 30. As best seen in FIG. 5, post 80 is cylindrical and includes a bottom end 82 secured to platform 78 and a top end 84 spaced below the upper surface 20 a suitable distance (e.g., about 0.010 inches) to prevent a typical tympanotomy vent tube (shown in phantom at 85 in FIG. 5) from sliding off the post when lid 18 covers the compartment.

In a preferred embodiment, the depth of the compartment 30 is about 0.25 inches, the raised portion or platform 78 forms a horizontal surface about 0.05 inches above the bottom wall 76 and post 80 has a height of about 0.240 inches and a diameter of about 0.039 inches, which is suitable for allowing passage of the post through the central opening of a typical tympanotomy vent tube with some clearance.

A groove 86 is formed in the surface 20 parallel with the front edge 22 of the tray and extends from lateral edge 26 to the outer side wall 75 of the compartment 30 opposite the post 80. The depth of the groove 86 increases in the direction of compartment 30, for example at an angle of declination Θ of about 13° relative to the bottom wall 76. The upper or outer end 88 of groove 86 terminates slightly below (e.g., about 0.022 inches) surface 20 and the inner or lower end 90 terminates below the top end 84 of post 80. The width of the groove 86 is suitably dimensioned (e.g., about 0.065 inches) for accommodating a conventional forceps as will be described in more detail below.

A tapered rib 92 extends from lateral edge 44 of lid 18 to ridge 52 and is configured to fit within groove 86 when lid 18 is closed against tray 12 to cover compartment 30.

Figure 6:
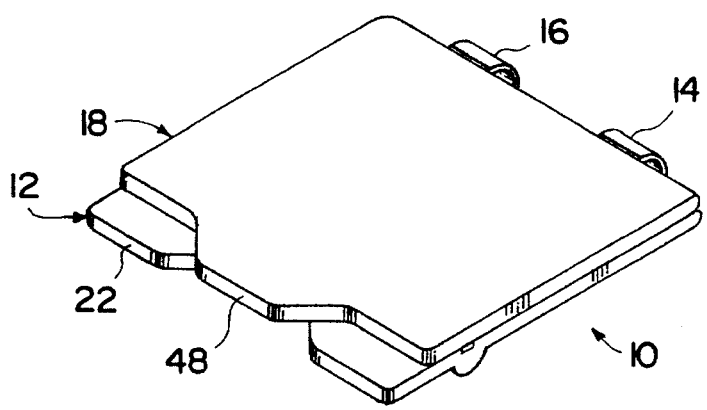
FIG. 6 is a perspective view of the package of FIG. 1 in a closed condition.
Figure 7:
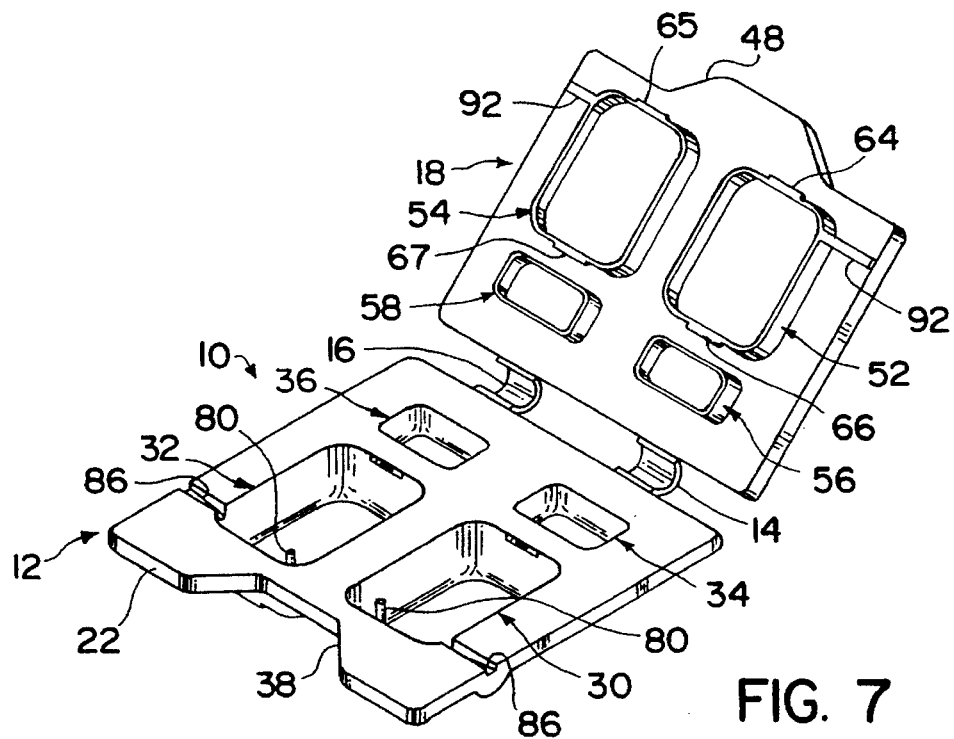
FIG. 7 is a perspective view of the package of FIG. 1 in an open condition.

In use, the package 10 is supplied in a closed condition, shown in FIG. 6, with lid 18 covering tray 12 and a tympanotomy vent tube 85 held on post 80 within the package in an upright position to locate one flange 87 in an exposed, easily graspable, upper position and the other opposing flange 89 in a lower position resting on platform 78. The tympanotomy vent tube can move up and down along the length of the post during transport, sterilization and delivery, but cannot fall off the post as long as the lid is closed against the tray. The sterile package 10 with a tympanotomy vent tube enclosed is opened by lifting the trapezoidal extension 48 of the lid 18 away from the tray 12. Lid 18 is normally biased away from the tray 12 as shown in FIG. 7 so that, once open, the package will remain open.

Figure 8:
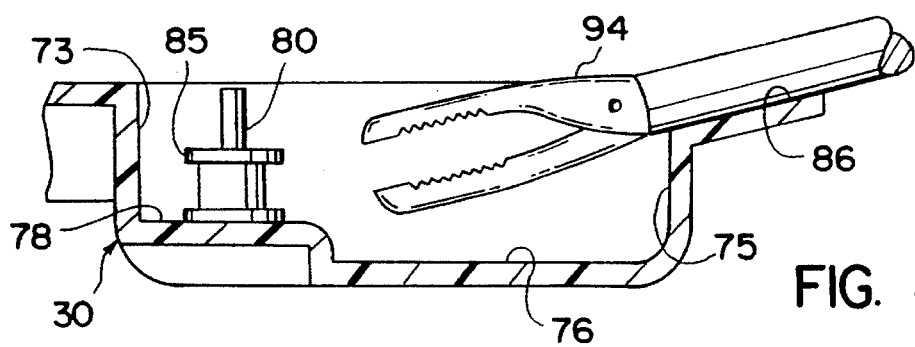
FIG. 8 is a fragmentary side view, partly in section, illustrating use of the package of the present invention.

In accordance with the present invention, the package 10 is held in a horizontal position when closed and the lid 18 opened to permit access to the compartments in the tray 12. The tympanotomy vent tube 85 is held on the post 80 in a vertical upright position, as shown in FIG. 8, with the flanges at opposed ends of the cylindrical vent tube body disposed in horizontal planes above the bottom wall 76 of the compartment 30. A grasping forceps 94 is maneuvered, usually by a nurse, to pick up the tympanotomy vent tube by placing the forceps in the groove 86 to align the forceps jaws with the tympanotomy vent tube and to guide the forceps to facilitate grasping the upper flange of the tympanotomy vent tube 85. The location of the post 80 within the compartment adjacent the inner side wall 73 provides sufficient space between the outer side wall 75 and the tympanotomy vent tube to accommodate the jaws of the forceps and to improve visualization of the grasping procedure. With the upper flange of the tympanotomy vent tube 85 firmly grasped by the forceps 94, the tympanotomy vent tube is lifted off of the post 80 such that the forceps can be used directly by the surgeon to insert the opposing, lower flange through a slit in the tympanic membrane to implant the tympanotomy vent tube. Accordingly, grasping of the tympanotomy vent tube is facilitated in a manner to expedite implanting of the tympanotomy vent tube in accordance with the present invention. Moreover, there is less risk of the tympanotomy vent tube falling out of the compartment or being improperly grasped, reducing the risk of contamination.

Figure 9:
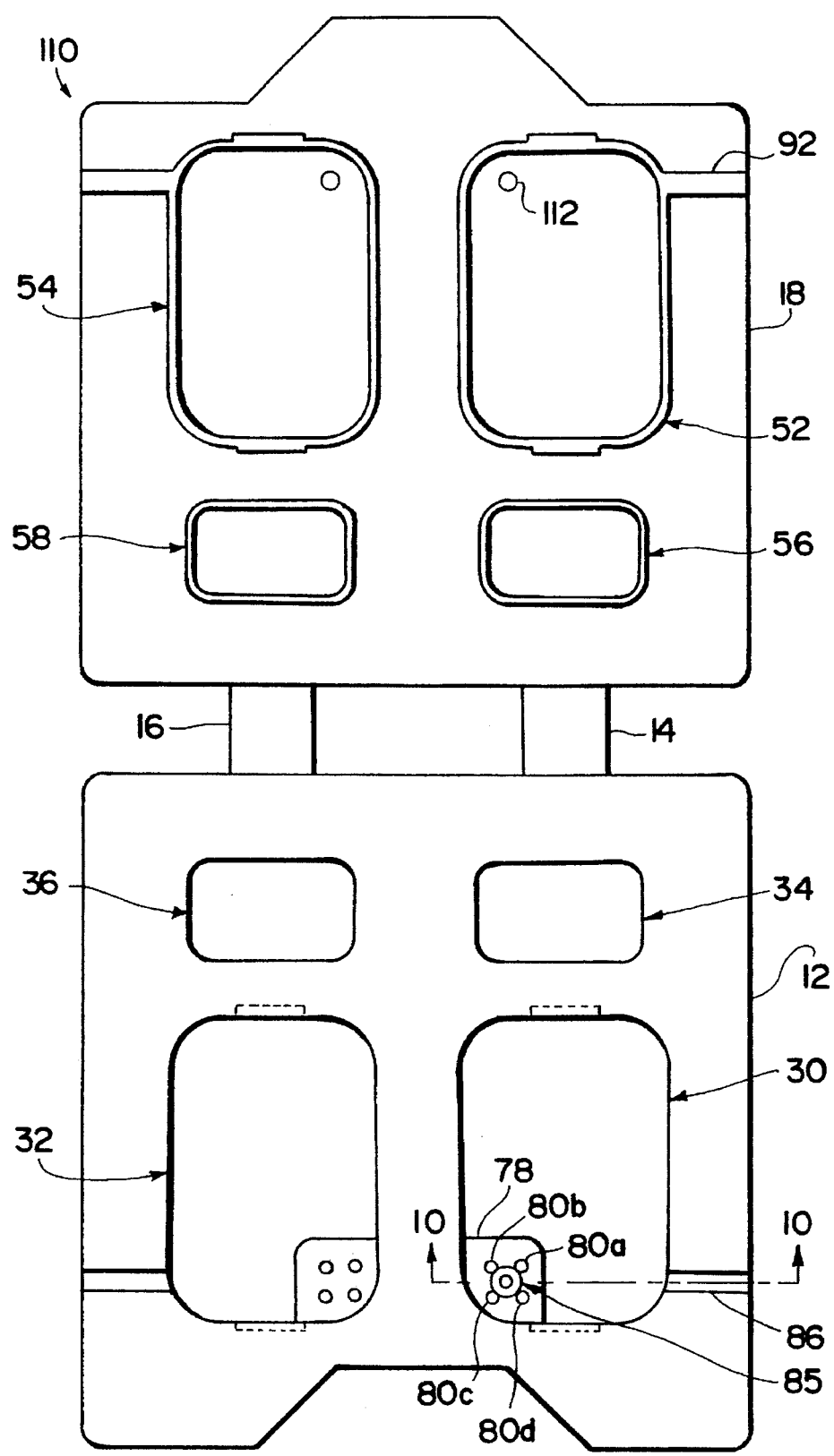
FIG. 9 is a flattened projection of a modified package according to the present invention.
Figure 10:
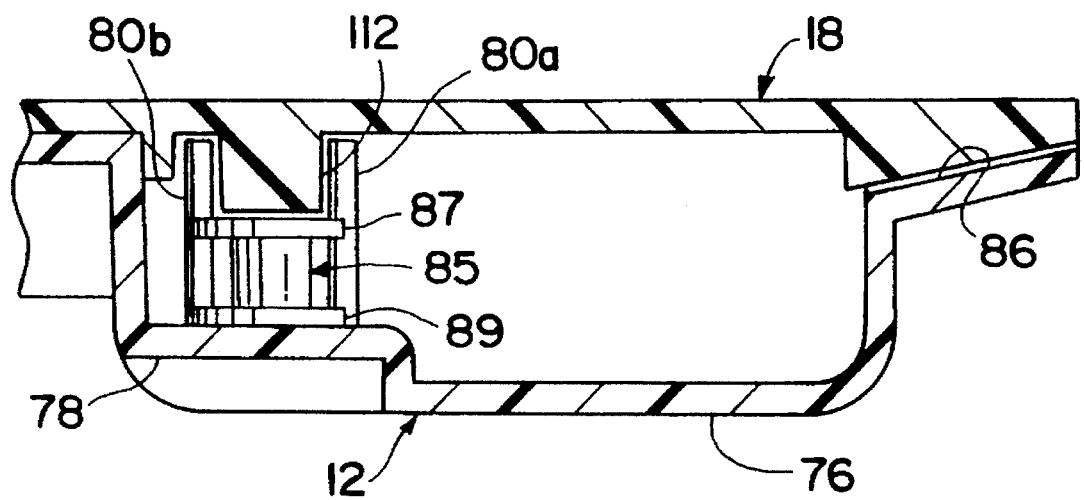
FIG. 10 is a cross-sectional view taken through line 10—10 in FIG. 9.

A modification of a package according to the present invention is illustrated in FIGS. 9 and 10. The modified package 110 is similar to the package 10 shown in FIG. 1 but with a plurality of posts 80a, 80b, 80c and 80d mounted perpendicularly on the platform 78 to define a cage for retaining a vent tube 85 in a substantially fixed, upright position within the compartment 30. Posts 80a, 80b, 80c and 80d are arranged in a square formation on platform 78 and are suitably spaced from one another to circumscribe upper and lower flanges 87 and 89 of the tube and to permit access to the tube with a forceps. As best seen in FIG. 10, movement of the vent tube 85 along the length of the posts can be limited by use of a cylindrical nub 112 carried or formed on the lid 18 in opposed relation to the space between posts 80a, 80b, 80c and 80d. When lid 18 is closed against the tray 12, nub 112 fits between the posts to serve as a stop or abutment preventing the vent tube 85 from migrating over the posts.

Figure 11:
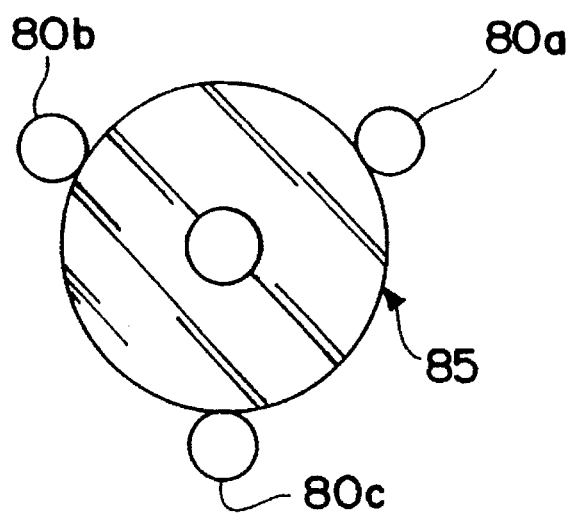
FIG. 11 is an enlarged fragmentary top view of an alternative post arrangement for the package of the present invention.

Although four posts are used to retain the vent tube in the package shown in FIG. 9, any number of posts can be used for this purpose. For example, in FIG. 11 a modification of a package according to the present invention is shown wherein three posts 80a, 80b and 80c are arranged in a triangular formation to retain a vent tube 85 in a substantially fixed position within a compartment.

From the above, it will be appreciated that the package of the present invention can be used for sterile delivery of small tubular implants such as vent tubes as well as other types of medical implants and devices. By "tubular" is meant having a passage formed partly or completely therethrough; and, when the package of the present invention is used for sterile delivery of a tubular device, the device can be retained in a substantially fixed position within a compartment of the package using any suitable retaining structure. For example, the device can be held on a post protruding from a bottom wall of the compartment, between plural posts forming a cage within the compartment, and/or within a recess or detent structure formed in the bottom wall of the compartment. Packages having plural posts, recesses and/or detents are also advantageous when used to deliver medical devices without suitable passages for receiving a post.

The posts of the present invention can be cylindrical as shown or have any other configuration in cross-section, including polygonal, elliptical and/or helical configurations, depending on their intended use and the type of device to be delivered. The posts are preferably long enough to prevent medical devices retained by the posts from migrating over the posts when the lids of the packages are closed. Alternatively, or in addition to providing long posts, projections or nubs can be carried or formed on the lid for cooperating with the posts to retain the medical devices.

Although two compartments have been shown and described herein as carrying posts, the package of the present invention can have any number of compartments carrying posts and can also combine compartments carrying posts with empty compartments of varying size and shape. The compartments can have any configuration in cross-section including circular, rectangular, and square configurations, and can have any length, width or depth suitable for accommodating a single type or various types of vent tubes and/or other medical devices.

It will also be appreciated that the posts of the present invention can be mounted at any position laterally spaced from an opposed outer wall of the compartment to accommodate jaws of a forceps. Further, multiple posts or groups of posts can be mounted within a single compartment; and, if desired, one or more of the posts or groups of posts can be aligned with grooves for guiding a forceps to medical devices held on or between the posts. The grooves can be horizontal or oriented at an angle relative to the bottom wall of a compartment and can have any size or shape to accommodate a forceps.

The package is preferably formed as a one-piece molded part using a medically-acceptable plastic material such as polypropylene but can be fabricated using other medically-acceptable materials and can be transparent or opaque, fabricated as separate parts and have any number of latching protrusions, detents and/or other suitable fasteners formed or attached at various locations for latching the lid to the tray. Furthermore, although the lid is shown and described herein as being hinged to the tray, it will be appreciated that other types of lids can be used, including detachable lids that are connected to the tray by detents or threaded engagement and lids that are slidably mounted on the tray for being selectively moved relative to the tray to cover and uncover the compartments.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. In combination, a medical implant and a package for sterile delivery of said medical implant, wherein said package comprises a tray defining a compartment having generally opposed sides and a bottom wall;

a lid configured to cover said compartment;

means for connecting said lid to said tray; and means for retaining said medical implant in a substantially fixed position within said compartment during transport and removal, said medical implant being spaced from one side of said compartment by said retaining means to define a space for accommodating jaws of a forceps.

2. A combination as recited in claim 1 wherein said medical implant includes a flange and said retaining means maintains said flange in a horizontal plane above said bottom wall of said compartment.

3. A combination as recited in claim 1 wherein said medical implant defines a passage and said retaining means includes a post extending from said bottom wall of said compartment into said passage.

4. A combination as recited in claim 1 wherein said retaining means includes a cage formed by a plurality of posts extending from said bottom wall of said compartment.

5. A combination as recited in claim 4 and further comprising a nub carried by said lid in opposed relation to said cage for holding said medical implant within said cage when said lid is closed against said tray.

6. A combination as recited in claim 1 wherein a groove is formed in said tray adjacent said one side of said compartment for aligning a forceps with said medical implant.

7. A combination as recited in claim 6 wherein said lid carries a rib configured to mate with said groove in said tray.

8. A combination as recited in claim 6 wherein said medical implant is located adjacent a side of said compartment opposite said groove and said groove is oriented toward said medical implant.

9. A combination as recited in claim 8 wherein said groove declines at an angle in the direction of said medical implant.

10. A combination as recited in claim 9 wherein said angle of declination is about 13°.

11. A combination as recited in claim 3 wherein said post has a length sufficient to prevent said medical implant from being dislodged when said lid covers said compartment.

12. A combination as recited in claim 1 wherein said tray defines a plurality of compartments, 13. A combination as recited in claim 1 wherein said compartment includes a platform spaced above said bottom wall and said medical implant is mounted on said platform, 14. A combination as recited in claim 1 wherein said package is molded as an integral one-piece assembly, 15. A combination as recited in claim 1 wherein said medical implant is a tympanotomy vent tube.

* * * * *